(12) United States Patent
Hull

(10) Patent No.: US 7,584,060 B2
(45) Date of Patent: Sep. 1, 2009

(54) INVERSE METHOD TO CALCULATE MATERIAL PROPERTIES USING AN INSERTION LOSS TEST

(75) Inventor: Andrew J. Hull, Portsmouth, RI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 163 days.

(21) Appl. No.: 11/769,106

(22) Filed: Jun. 27, 2007

(65) Prior Publication Data

US 2009/0000380 A1  Jan. 1, 2009

(51) Int. Cl.
*G01N 29/04* (2006.01)
(52) U.S. Cl. .............. 702/33; 702/30; 702/65; 702/113; 73/760; 73/596; 73/579; 73/658; 73/662; 73/663; 324/663; 324/687; 324/688; 324/690
(58) Field of Classification Search ............... 702/30, 702/33, 65, 182, 56, 108, 115, 114, 113; 73/760, 596, 73, 74, 61.48, 61.49, 579, 658, 73/659, 660, 662, 663; 700/29, 299; 324/663, 324/687, 688, 690, 228; 374/53, 54
See application file for complete search history.

(56) References Cited

U.S. PATENT DOCUMENTS

| | | | | |
|---|---|---|---|---|
| 5,121,629 A | * | 6/1992 | Alba | 73/61.41 |
| 5,223,796 A | * | 6/1993 | Waldman et al. | 324/687 |
| 5,900,736 A | * | 5/1999 | Sovik et al. | 324/663 |
| 6,941,231 B2 | * | 9/2005 | Zeroug et al. | 702/39 |
| 7,010,981 B1 | * | 3/2006 | Hull | 73/602 |
| 7,062,386 B1 | * | 6/2006 | Hull | 702/39 |
| 7,219,024 B2 | * | 5/2007 | Gamache et al. | 702/65 |
| 7,451,657 B2 | * | 11/2008 | Goldfine et al. | 73/760 |
| 2004/0054474 A1 | * | 3/2004 | Zeroug et al. | 702/1 |
| 2005/0171703 A1 | * | 8/2005 | Goldfine et al. | 702/30 |
| 2006/0009865 A1 | * | 1/2006 | Goldfine et al. | 700/29 |

* cited by examiner

*Primary Examiner*—Carol S Tsai
(74) *Attorney, Agent, or Firm*—James M. Kasischke; Michael P. Stanley; Jean-Paul A. Nasser

(57) ABSTRACT

A method for calculating material properties of a material includes conducting two insertion loss tests of the material having a single thickness and a double thickness. These tests are conducted at a zero wavenumber. Utilizing these insertion loss tests, a dilatational wavespeed is computed. The method continues by calculating a shear wavespeed by performing three insertion loss tests of the material at single, double and triple thicknesses. These tests are conducted at a non-zero wavenumber. A shear wavespeed can be calculated from the dilatational wavespeed and these insertion loss tests. Lamé constants, Young's modulus, Poisson's ratio, and the shear modulus for the material of interest can then be calculated using the dilatational and shear wavespeeds.

18 Claims, 13 Drawing Sheets

INVERSE METHOD TO CALCULATE MATERIAL PROPERTIES USING AN INSERTION LOSS TEST

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER RELATED APPLICATIONS

None.

BACKGROUND OF THE INVENTION (1) Field of the Invention

The present invention relates to material properties measurement and, more particularly, to a method for measuring material properties using wall displacement measurements recorded during an insertion loss experiment.

(2) Description of the Prior Art

Insertion loss is a common measurement that is used to determine how effective a piece of material attenuates acoustic energy at a specific frequency. Insertion loss is calculated by projecting acoustic energy at piece of material and measuring the pressure on the projector side and the opposite side of the material, normally with hydrophones.

FIG. 1 depicts a typical setup for insertion loss. Sound pressure is transmitted to a test sample 10 by an acoustic projector 12. Acoustic projector 12 can transmit an acoustic wave at a preset frequency. Using a 1 m by 1 m specimen, the minimum frequency is about 10 kHz. A first hydrophone 14 is positioned on the opposite side of the sample 10 to measure the transmitted pressure. The ratio of the source pressure to the transmitted pressure expressed in decibels is the insertion loss of the material. A second hydrophone 16 is positioned on the same side of sample 10 as projector 12 to measure the reflected acoustic pressure.

Insertion loss can also be determined by measuring the motion of the test sample with either accelerometers or laser velocimeters and calculating the pressure field based on conservation of linear momentum. In the test setup shown here, a first laser velocimeter 18 is used to measure the acceleration and position of a first side 20 of sample 10. A second laser velocimeter 22 is used to measure the acceleration and position of a second side 24 of sample 10. Laser velocimeters 18, 22 are preferred because accelerometers must be positioned on sample 10 and might interfere with the measurements. The projector 12 angle θ relative to the test material can be changed so that the effects of acoustic energy at varying angles can be studied. Changing the excitation angle θ is equivalent to changing the excitation wavenumber. Thus, the two parameters that are typically varied during this test are frequency and wavenumber.

For underwater applications, the material is submerged in a fluid (normally water), and an underwater speaker or projector transmits energy at the material; however, a gaseous environment could be used. Because this test is only interested in acoustic attenuation of the material, the height and width of the test specimen are large compared to its thickness. In view of this, the test specimen should have a thickness between 10 mm and 100 mm. This prevents acoustic energy from moving around the specimen and contaminating the transmitted pressure field and interacting with the opposite side to the test specimen. The test is also dependent on the environment where it is conducted. Small test tanks prevent low frequency measurements due to reflection and reverberation of the acoustic energy. These are, however, practical limitations and do not enter into this theoretical analysis.

SUMMARY OF THE INVENTION

One object of this invention is to accurately determine the material properties of a sample in an insertion loss experiment.

Another object of the present invention is to determine the material properties of dilatational wavespeed, shear wavespeed, Lamé constants, Young's modulus, and shear modulus of a material of interest.

The present invention features an inverse method where normal wall movement measurements obtained during an insertion loss test are combined to equal material properties. This allows for the calculation of Young's modulus, shear modulus, and Poisson's ratio from an insertion loss test. Alternatively, Lame constants and Poisson's ratio or complex dilatational and shear wavespeeds are also obtainable from this method. For dilatational wave energy, the test requires two material samples, one being twice as thick as the other. For shear wave energy, the test requires three material samples, one being twice as thick as the first and the second being three times as thick as the first. Measurements of these multiple samples allow the governing equations and test data be combined in a manner that results in an inverse method in which the material properties are closed form solutions of the measurement data. This is sometimes referred to as a linear inverse method.

BRIEF DESCRIPTION OF THE DRAWINGS

These and other features and advantages of the present invention will be better understood in view of the following description of the invention taken together with the drawings wherein.

DETAILED DESCRIPTION OF THE INVENTION

Figure 1:
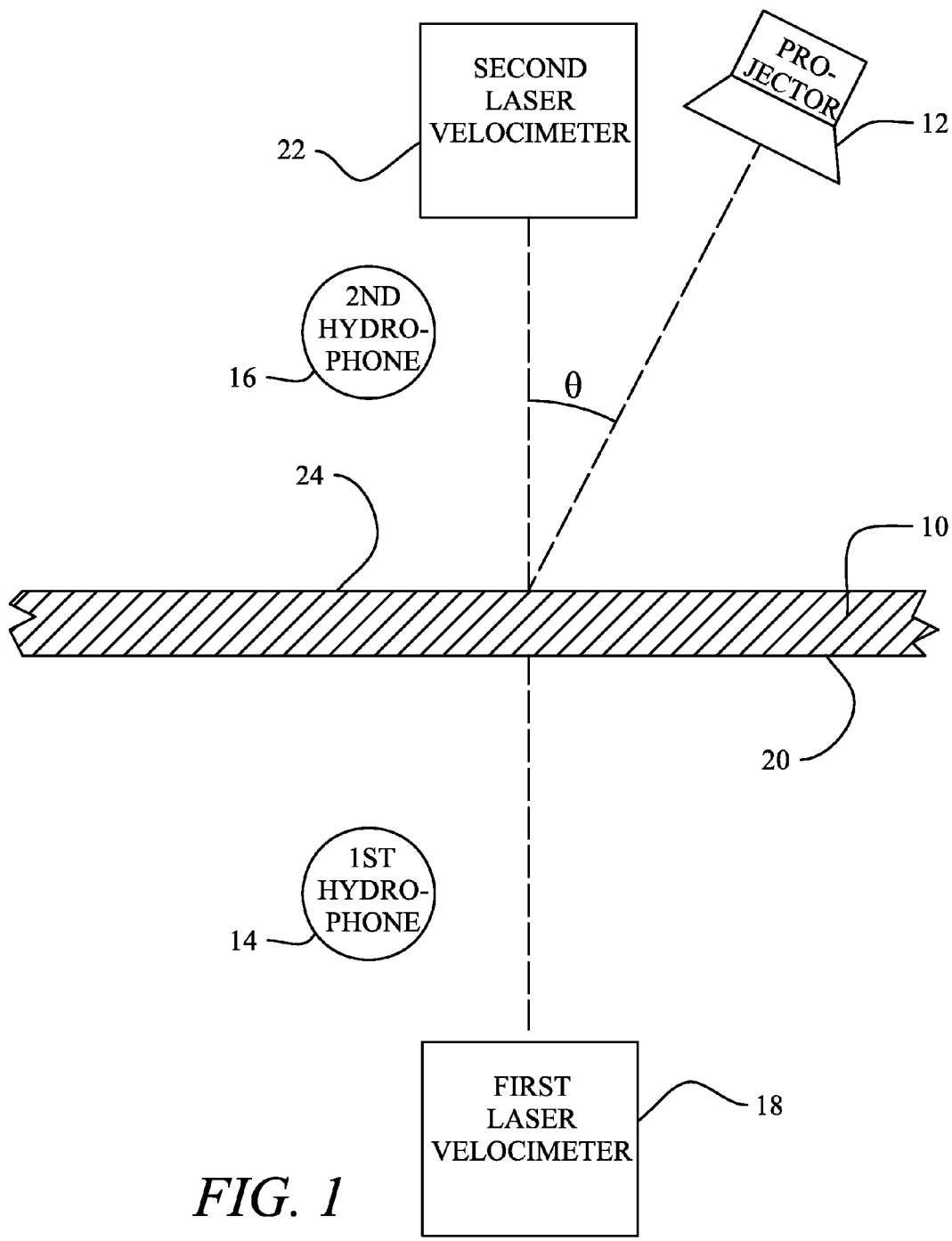
FIG. 1 is a diagram of the test setup for the current invention.
Figure 2:
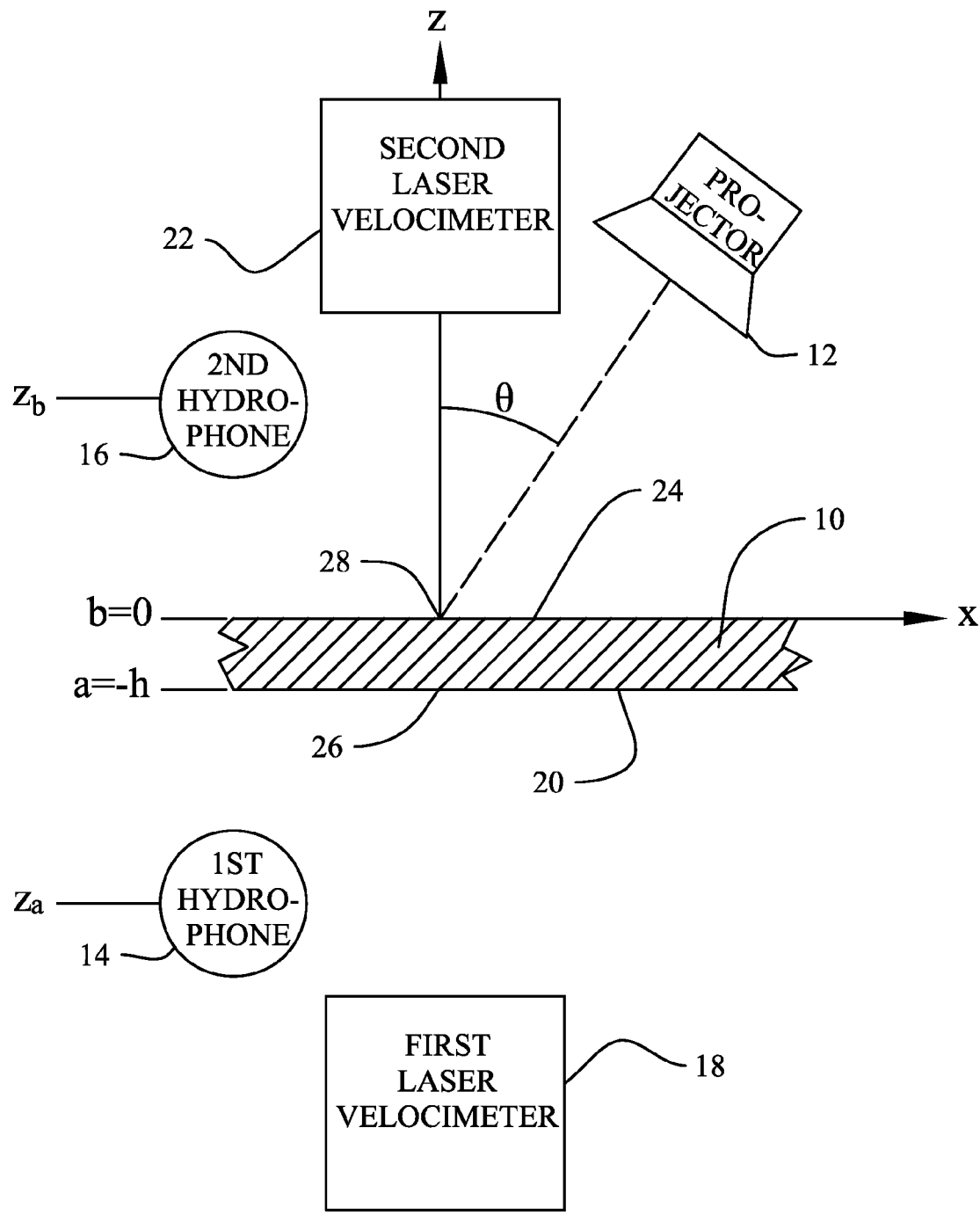
FIG. 2 is a diagram showing the coordinate system used by the current invention.

The coordinate system of the test configuration is shown in FIG. 2. Projector 12 is oriented at an angle θ with respect to sample 10. A first measurement location 28 is located on the far side of sample 10 from projector 12. This is the position where the beam from laser velocimeter 18 shown in FIG. 1 contacts surface 20. A second measurement location 26 corresponds to where second laser velocimeter 22 beam contacts surface 24. Under the coordinate system, the z axis is orthogonal to the second surface of sample 10 with the origin at this surface. Note that using this orientation results in b=0 and a having a value less than zero (−h). The thickness of the sample, h, is a positive value. The y axis is oriented into the page.

The system model has three governing differential equations that are coupled at their interfaces using conservation of linear momentum. The acoustic pressure in the fluid on the projector side of the test specimen is governed by the wave equation and is written in Cartesian coordinates as [1]

$$\frac{\partial^2 p_1(x,z,t)}{\partial z^2} + \frac{\partial^2 p_1(x,z,t)}{\partial x^2} - \frac{1}{c_f^2}\frac{\partial^2 p_1(x,z,t)}{\partial t^2} = 0, \quad (1)$$

where $p_1(x,z,t)$ is the pressure (N/m$^2$), z is the spatial location (m) normal to the plate, x is spatial location along the plate (m), $c_f$ is the compressional wavespeed of the fluid (m/s), t is time (s), and the subscript one denotes the area on the projector side of the test material. The motion of the material is governed by the equation [2]

$$\mu\nabla^2 u + (\lambda+\mu)\nabla\nabla\cdot u = \rho\frac{\partial^2 u}{\partial t^2}, \quad (2)$$

where ρ is the density (kg/m$^3$), λ and μ are the complex Lamé constants (N/m$^2$), • denotes a vector dot product; u is the Cartesian coordinate displacement vector of the material. The acoustic pressure in the fluid on opposite the projector side of the test specimen is governed by the wave equation and is written in Cartesian coordinates as $$\frac{\partial^2 p_2(x,z,t)}{\partial z^2} + \frac{\partial^2 p_2(x,z,t)}{\partial x^2} - \frac{1}{c_f^2}\frac{\partial^2 p_2(x,z,t)}{\partial t^2} = 0, \quad (3)$$

where $p_2(x,z,t)$ is the pressure (N/m$^2$) and the subscript two denotes the area opposite the projector side of the test material. The interface between the first fluid and solid surface of the material at z=b satisfies the linear momentum equation, which is [3]

$$\rho_f\frac{\partial^2 u_z(x,b,t)}{\partial t^2} = -\frac{\partial p_1(x,b,t)}{\partial z}, \quad (4)$$

where $\rho_f$ is the density of the fluid (kg/m$^3$). The interface between the second fluid and solid surface of the material at z=a also satisfies the linear momentum equation, and is written as $$\rho_f\frac{\partial^2 u_z(x,a,t)}{\partial t^2} = -\frac{\partial p_2(x,a,t)}{\partial z}. \quad (5)$$

The above five equations are the governing partial differential equations of the insertion loss experiment.

Equations (1)-(3) are now transformed from partial differential equations into ordinary differential equations and then into algebraic expressions. The acoustic pressure in equation (1) is modeled as a function at definite wavenumber and frequency as $$p_1(x,z,t) = P_1(z,k_x,\omega)\exp(ik_x x)\exp(i\omega t), \quad (6)$$

where ω is frequency (rad/s), $k_x$ is the spatial wavenumber in the x direction (rad/m), and i is the square root of −1. The spatial wavenumber is given by $$k_x = \frac{\omega}{c_f}\sin(\theta), \quad (7)$$

where θ is the angle of incidence (rad) of the incoming acoustic wave with θ=0 corresponding to excitation normal to the sample (or broadside excitation). Inserting equation (6) into equation (1) and solving the resulting ordinary differential equation yields $$P_1(z,k_x,\omega) = H(k_x,\omega)\exp(i\gamma z) + P_S(\omega)\exp(-i\gamma z). \quad (8)$$

In equation (8), the first term on the right hand side represents the reradiated (or reflected) pressure field and the second term represents the applied incident pressure field (the forcing function) acting on the structure. The term $H(k_x,\omega)$ is the wave propagation coefficient of the reflected pressure field and the term $P_S(\omega)$ is the source (or excitation) level. Additionally, $$\gamma = \sqrt{\left(\frac{\omega}{c_f}\right)^2 - k_x^2}, \quad (9)$$

where γ is the wavenumber of the acoustic pressure in the fluid.

Equation (2) is manipulated by writing the Cartesian coordinate displacement vector u as $$u = \begin{Bmatrix} u_x(x,y,z,t) \\ u_y(x,y,z,t) \\ u_z(x,y,z,t) \end{Bmatrix}, \quad (10)$$

with y denoting the direction into the material in FIG. 2. The symbol $\nabla$ is the gradient vector differential operator written in three-dimensional Cartesian coordinates as [4]

$$\nabla = \frac{\partial}{\partial x}i_x + \frac{\partial}{\partial y}i_y + \frac{\partial}{\partial z}i_z, \tag{11}$$

with $i_x$ denoting the unit vector in the x-direction, $i_y$ denoting the unit vector in the y-direction, and $i_z$ denoting the unit vector in the z-direction; $\nabla^2$ is the three-dimensional Laplace operator operating on vector u as $$\nabla^2 u = \nabla^2 u_x i_x + \nabla^2 u_y i_y + \nabla^2 u_z i_z, \tag{12}$$

with $\nabla^2$ operating on scalar u as $$\nabla^2 u_{x,y,z} = \nabla \cdot \nabla u_{x,y,z} = \frac{\partial^2 u_{x,y,z}}{\partial x^2} + \frac{\partial^2 u_{x,y,z}}{\partial y^2} + \frac{\partial^2 u_{x,y,z}}{\partial z^2}; \tag{13}$$

and the term $\nabla \cdot u$ is called the divergence and is equal to $$\nabla \cdot u = \frac{\partial u_x}{\partial x} + \frac{\partial u_y}{\partial y} + \frac{\partial u_z}{\partial z}. \tag{14}$$

The displacement vector u is written as $$u = \nabla \phi + \nabla \times \vec{\psi}, \tag{15}$$

where $\phi$ is a dilatational scalar potential, $\times$ denotes a vector cross product, and $\vec{\psi}$ is an equivoluminal vector potential expressed as $$\vec{\Psi} = \begin{Bmatrix} \Psi_x(x, y, z, t) \\ \Psi_y(x, y, z, t) \\ \Psi_z(x, y, z, t) \end{Bmatrix}. \tag{16}$$

The structural problem is formulated as a two-dimensional response ($y \equiv 0$ and $\partial(\cdot)/\partial y \equiv 0$) problem. Expanding equation (15) and breaking the displacement vector into its individual nonzero terms yields $$u_x(x, z, t) = \frac{\partial \phi(x, z, t)}{\partial x} - \frac{\partial \psi_y(x, z, t)}{\partial z} \tag{17}$$

and $$u_z(x, z, t) = \frac{\partial \phi(x, z, t)}{\partial z} + \frac{\partial \psi_y(x, z, t)}{\partial x}. \tag{18}$$

Equations (17) and (18) are next inserted into equation (2), which results in $$c_d^2 \nabla^2 \phi(x, z, t) = \frac{\partial^2 \phi(x, z, t)}{\partial t^2} \tag{19}$$

and $$c_s^2 \nabla^2 \psi_y(x, z, t) = \frac{\partial^2 \psi_y(x, z, t)}{\partial t^2} \tag{20}$$

where equation (19) corresponds to the dilatational component and equation (20) corresponds to the shear component of the displacement field [5]. Correspondingly, the constants $c_d$ and $c_s$ are the complex dilatational and shear wave speeds, respectively, and are determined by $$c_d = \sqrt{\frac{\lambda + 2\mu}{\rho}} \tag{21}$$

and $$c_s = \sqrt{\frac{\mu}{\rho}}. \tag{22}$$

The relationship of the Lamé constants to the compressional and shear moduli is shown as $$\lambda = \frac{E\upsilon}{(1+\upsilon)(1-2\upsilon)} \tag{23}$$

and $$\mu = G = \frac{E}{2(1+\upsilon)}, \tag{24}$$

where E is the complex Young's (compressional) modulus (N/m$^2$), G is the complex shear modulus (N/m$^2$), and $\upsilon$ is the Poisson's ratio of the material (dimensionless).

The conditions of infinite length and steady-state response are now imposed, allowing the scalar and vector potential to be written as $$\phi(x,z,t) = \Phi(z)\exp(ik_x x)\exp(i\omega t), \tag{25}$$

and $$\psi_y(x,z,t) = \Psi(z)\exp(ik_x x)\exp(i\omega t). \tag{26}$$

Inserting equation (25) into equation (19) yields $$\frac{d^2 \Phi(z)}{dz^2} + \alpha^2 \Phi(z) = 0, \tag{27}$$

where $$\alpha = \sqrt{k_d^2 - k_x^2}, \tag{28}$$

and $$k_d = \frac{\omega}{c_d}. \tag{29}$$

Inserting equation (26) into equation (20) yields $$\frac{d^2 \Psi(z)}{dz^2} + \beta^2 \Psi(z) = 0, \tag{30}$$

where

-continued $$\beta = \sqrt{k_s^2 - k_x^2}, \quad (31)$$

and $$k_s = \frac{\omega}{c_s}. \quad (32)$$

The solution to equation (27) is $$\Phi(z) = A(k_x,\omega)\exp(i\alpha z) + B(k_x,\omega)\exp(-i\alpha z), \quad (33)$$

and the solution to equation (30) is $$\Psi(z) = C(k_x,\omega)\exp(i\beta z) + D(k_x,\omega)\exp(-i\beta z), \quad (34)$$

where $A(k_x,\omega)$, $B(k_x,\omega)$, $C(k_x,\omega)$, and $D(k_x,\omega)$ are wave propagation constants that are determined below. The displacements can now be written as functions of the unknown constants using the expressions in equations (17) and (18). They are $$\begin{aligned} u_z(x,z,t) &= U_z(k_x,z,\omega)\exp(ik_x x)\exp(i\omega t) \\ &= \{i\alpha[A(k_x,\omega)\exp(i\alpha z) - B(k_x,\omega)\exp(-i\alpha z)] + \\ &\quad ik_x[C(k_x,\omega)\exp(i\beta z) + D(k_x,\omega)\exp(-i\beta z)]\} \\ &\quad \exp(ik_x x)\exp(i\omega t), \end{aligned} \quad (35)$$

and $$\begin{aligned} u_x(x,z,t) &= U_x(k_x,z,\omega)\exp(ik_x x)\exp(i\omega t) \\ &= \{ik_x[A(k_x,\omega)\exp(i\alpha z) + B(k_x,\omega)\exp(-i\alpha z)] - \\ &\quad i\beta[C(k_x,\omega)\exp(i\beta z) - D(k_x,\omega)\exp(-i\beta z)]\} \\ &\quad \exp(ik_x x)\exp(i\omega t). \end{aligned} \quad (36)$$

The normal stress the top of the plate (z=b) is equal to opposite the pressure in the fluid. This expression is $$\tau_{zz}(x,b,t) = (\lambda+2\mu)\frac{\partial u_z(x,b,t)}{\partial z} + \lambda\frac{\partial u_x(x,b,t)}{\partial x} = -p_1(x,b,t), \quad (37)$$

and the tangential stress at the top of the plate is zero and this equation is written as $$\tau_{zx}(x,b,t) = \mu\left[\frac{\partial u_x(x,b,t)}{\partial z} + \frac{\partial u_z(x,b,t)}{\partial x}\right] = 0. \quad (38)$$

The normal stress the bottom of the plate (z=a) is equal to opposite the pressure in the fluid. This expression is $$\tau_{zz}(x,a,t) = (\lambda+2\mu)\frac{\partial u_z(x,a,t)}{\partial z} + \lambda\frac{\partial u_x(x,a,t)}{\partial x} = -p_2(x,a,t), \quad (39)$$

and the tangential stress at the bottom of the plate is zero and this equation is written as $$\tau_{zx}(x,a,t) = \mu\left[\frac{\partial u_x(x,a,t)}{\partial z} + \frac{\partial u_z(x,a,t)}{\partial x}\right] = 0, \quad (40)$$

where $p_2(x,b,t)$ in equation (39) represents the radiated acoustic pressure in the fluid load on the opposite side of the acoustic projector.

The acoustic pressure in equation (3) is modeled as a function at definite wavenumber and frequency as $$p_2(x,z,t) = P_2(z,k_x,\omega)\exp(ik_x x)\exp(i\omega t), \quad (41)$$

Inserting equation (41) into equation (3) and solving the resulting ordinary differential equation yields $$P_2(z,k_x,\omega) = K(k_x,\omega)\exp(-i\gamma z), \quad (42)$$

which is the outgoing (or transmitted) acoustic energy in the second fluid. The term $K(k_x,\omega)$ is the wave propagation coefficient of the transmitted pressure field. Note that there is no incoming wave energy on this side of the test specimen and thus only one exponential term is present.

Assembling equations (1)-(42) and letting b=0 yields the four-by-four system of linear equations that model the system. They are $$Ax = b, \quad (43)$$

where the entries of equation (43) are $$A_{11s} = -\alpha^2\lambda - 2\alpha^2\mu - \lambda k_x^2, \quad (44)$$

$$A_{11f} = \frac{\rho_f \omega^2 \alpha}{\gamma}, \quad (45)$$

$$A_{11} = A_{11s} + A_{11f}, \quad (46)$$

$$A_{12} = A_{11s} - A_{11f}, \quad (47)$$

$$A_{13s} = 2k_x\beta\mu, \quad (48)$$

$$A_{13f} = \frac{\rho_f \omega^2 k_x}{\gamma}, \quad (49)$$

$$A_{13} = -A_{13s} + A_{13f}, \quad (50)$$

$$A_{14} = A_{13s} + A_{13f}, \quad (51)$$

$$A_{21} = -2\mu k_x \alpha, \quad (52)$$

$$A_{22} = -A_{21}, \quad (53)$$

$$A_{23} = \mu\beta^2 - \mu k_x^2, \quad (54)$$

$$A_{24} = A_{23}, \quad (55)$$

$$A_{31} = (A_{11s} - A_{11f})\exp(i\alpha a), \quad (56)$$

$$A_{32} = (A_{11s} + A_{11f})\exp(-i\alpha a), \quad (57)$$

$$A_{33} = (-A_{13s} - A_{13f})\exp(i\beta a), \quad (58)$$

$$A_{34} = (A_{13s} - A_{13f})\exp(-i\beta a), \quad (59)$$

$$A_{41} = A_{21}\exp(i\alpha a), \quad (60)$$

$$A_{42} = -A_{21}\exp(-i\alpha a), \quad (61)$$

$$A_{43} = A_{23}\exp(i\beta a), \quad (62)$$

$$A_{44} = A_{23}\exp(-i\beta a), \quad (63)$$

$$x_{11} = A(k_x, \omega), \quad (64)$$

$$x_{21} = B(k_x, \omega), \quad (65)$$

$$x_{31} = C(k_x, \omega), \quad (66)$$

$$x_{41} = D(k_x, \omega), \quad (67)$$

$$b_{11} = -2P_S(\omega), \quad (68)$$

$$b_{21} = 0, \quad (69)$$

$$b_{31} = 0, \quad (70)$$

and $$b_{41} = 0. \quad (71)$$

It is noted that the subscript s corresponds to terms related to the structure and the subscript f corresponds to terms related to the fluid. Using equations (43)-(71) the solution to the constants $A(k_x,\omega)$, $B(k_x,\omega)$, $C(k_x,\omega)$ and $D(k_x,\omega)$ can be calculated at each specific wavenumber and frequency. Written in transfer function form with reference to the source excitation level, they are $$\frac{A(k_x, \omega)}{P_S(\omega)} = \{4A_{13s}A_{22}A_{23}[1 - \cos(\beta a)\exp(i\alpha a)] - Ai(A_{11}A_{23}^2 + A_{13f}A_{22}A_{23})\sin(\beta a)\exp(-i\alpha a)\}\Delta^{-1}, \quad (72)$$

$$\frac{B(k_x, \omega)}{P_S(\omega)} = \{4A_{13s}A_{22}A_{23}[1 - \cos(\beta a)\exp(i\alpha a)] + 4i(A_{12}A_{23}^2 - A_{13f}A_{22}A_{23})\sin(\beta a)\exp(i\alpha a)\}\Delta^{-1}, \quad (73)$$

$$\frac{C(k_x, \omega)}{P_S(\omega)} = \{4A_{11s}A_{22}A_{23}[-1 + \cos(\alpha a)\exp(-i\beta a)] - 4i(A_{13}A_{22}^2 + A_{11f}A_{22}A_{23})\sin(\alpha a)\exp(-i\beta a)\}\Delta^{-1}, \quad (74)$$

and $$\frac{D(k_x, \omega)}{P_S(\omega)} = \{4A_{11s}A_{22}A_{23}[1 - \cos(\alpha a)\exp(i\beta a)] + 4i(A_{14}A_{22}^2 + A_{11f}A_{22}A_{23})\sin(\alpha a)\exp(i\beta a)\}\Delta^{-1}, \quad (75)$$

where $$\Delta = \Delta_1 + \Delta_2 + \Delta_3 + \Delta_4 + \Delta_5, \quad (76)$$

$$\Delta_1 = \exp(-i\alpha a)\exp(i\beta a)(A_{11}A_{23} + A_{14}A_{22})^2, \quad (77)$$

$$\Delta_2 = -\exp(-i\alpha a)\exp(-i\beta a)(A_{11}A_{23} + A_{13}A_{22})^2, \quad (78)$$

$$\Delta_3 = -\exp(i\alpha a)\exp(i\beta a)(A_{12}A_{23} - A_{14}A_{22})^2, \quad (79)$$

$$\Delta_4 = \exp(i\alpha a)\exp(-i\beta a)(A_{12}A_{23} - A_{13}A_{22})^2, \quad (80)$$

and $$\Delta_5 = -8A_{11s}A_{13s}A_{22}A_{23}. \quad (81)$$

The transfer function between the wall motion in the z direction at z=a and the wall motion in the z direction at z=b (=0) is now written using equations (35), (72), (73), (74), and (75). Additionally, the individual terms from the matrix A are inserted into the expression resulting in $$T_{ba}(k_x, \omega) = \frac{U_z(k_x, b, \omega)}{U_z(k_x, a, \omega)} \quad (82)$$

$$= \frac{\kappa_1(k_x, \omega)\sin(\alpha a)\cos(\beta a) + [\kappa_2(k_x, \omega)\cos(\alpha a) + \kappa_3(k_x, \omega)\sin(\alpha a)]\sin(\beta a)}{\kappa_1(k_x, \omega)\sin(\alpha a) + \kappa_2(k_x, \omega)\sin(\beta a)},$$

where $$\kappa_1(k_x, \omega) = i\gamma(4\rho\beta\alpha k_x^2\omega^2), \quad (83)$$

$$\kappa_2(k_x, \omega) = i\gamma(\omega^2\rho - 2\mu k_x^2)(\beta^4 - k_x^4), \quad (84)$$

and $$\kappa_3(k_x, \omega) = -\alpha\rho_r\omega^2(\beta^4 + 2\beta^2 k_x^2 + k_x^4). \quad (85)$$

Further manipulation of equation (82) results in $$T_{ba}(k_x, \omega) = \frac{U_z(k_x, b, \omega)}{U_z(k_x, a, \omega)} \quad (86)$$

$$= \frac{\sin(\alpha a)\cos(\beta a) + [M(k_x, \omega)\cos(\alpha a) + N(k_x, \omega)\sin(\alpha a)]\sin(\beta a)}{\sin(\alpha a) + M(k_x, \omega)\sin(\beta a)},$$

where $$M(k_x, \omega) = \frac{\kappa_2(k_x, \omega)}{\kappa_1(k_x, \omega)}, \quad (87)$$

and $$N(k_x, \omega) = \frac{\kappa_3(k_x, \omega)}{\kappa_1(k_x, \omega)}. \quad (88)$$

Equations (86), (87), and (88) are a mathematical model of the ratio of wall motion of the test specimen. These equations are written so that the transfer function (or experimental data) is a function of material properties. They will be combined in such a manner that the material properties become functions of the experimental data. This process is explained in the next section.

For completeness, it is noted that the reflected acoustic field on the projector side is $$P_R(k_x, \omega) = \left[\left(\frac{\omega^2\rho_f}{i\gamma}\right)U_z(k_x, b, \omega) + 1\right]\exp(i\gamma z_b). \quad (89)$$

where $z_b$ is the position where the field is evaluated (m). The total pressure field on the projector side is a sum of the reflected field and the phase shifted source level written as $$P_{Total}(k_x,\omega) = P_R(k_x,\omega) + P_S(\omega)\exp(-i\gamma z_b). \quad (90)$$

The transmitted pressure field on the opposite side of the projector is $$P_T(k_x, \omega) = \left[\left(\frac{-\omega^2\rho_f}{i\gamma}\right)U_z(k_x, a, \omega)\right]\exp(-i\gamma z_a). \quad (91)$$

where $z_a$ is the position where the field is evaluated (m). The insertion loss is then calculated using $$IL(k_x, \omega) = 20\log_{10}\left[\frac{P_S(\omega)}{P_T(k_x, \omega)}\right]. \quad (92)$$

where $IL(k_x,\omega)$ is in units of decibels. These measurements are not necessary for the calculation of material properties according to the invention. $z_a$ and $z_b$ are the positions of hydrophones 14 and 16.

Applicant's measurement method is a two step method. In the first step, projector 12 provides acoustic waves to the sample at zero wavenumber. In view of equation (7), this means that the projector is oriented to provide acoustic waves at an angle θ of 0. In the second step, projector 12 provides acoustic waves to the sample at a non-zero wavenumber. This means that the projector is oriented to project acoustic waves at any angle θ other than 0.

The first part of the measurement method involves insonifying two separate pieces of the material at zero wavenumber. The second piece of material is twice as thick as the first piece of material. For zero wavenumber, equation (82) reduces to $$T_{ba}(0, \omega) = \frac{U_z(0, b, \omega)}{U_z(0, a, \omega)} = \cos(\alpha a) + \alpha\left[\frac{i\rho_f c_f}{\omega\rho}\right]\sin(\alpha a) = T_1(\omega), \quad (93)$$

and, written to correspond to the to the test piece that is twice as thick, becomes $$T_{b2a}(0, \omega) = \frac{U_z(0, b, \omega)}{U_z(0, 2a, \omega)} = \cos(2\alpha a) + \alpha\left[\frac{i\rho_f c_f}{\omega\rho}\right]\sin(2\alpha a) = T_2(\omega). \quad (94)$$

where $T_1(\omega)$ and $T_2(\omega)$ are the transfer function data from the experiment. It is noted, based on examination of equations (93) and (94), that no shear energy is excited in the structure when excitation is at zero wavenumber. Equations (93) and (94) can be combined and reduced using a double angle trigonometric expression to yield $$\cos(\alpha h) = \frac{T_2(\omega) + 1}{2T_1(\omega)} = \phi, \quad (95)$$

where φ is typically a complex valued number and h is the thickness of the first specimen (m). Equation (95) can be expanded into real and imaginary parts and solved, resulting in a value for α at every frequency in which a measurement is made. The solution to the real part of α is $$\text{Re}(\alpha) = \begin{cases} \frac{1}{2h}\text{Arccos}(s) + \frac{n\pi}{2h} & n \text{ even} \\ \frac{1}{2h}\text{Arccos}(-s) + \frac{n\pi}{2h} & n \text{ odd} \end{cases}, \quad (96)$$

where $$s = [\text{Re}(\phi)]^2 + [\text{Im}(\phi)]^2 - \sqrt{\{[\text{Re}(\phi)]^2 + [\text{Im}(\phi)]^2\}^2 - \{2[\text{Re}(\phi)]^2 - 2[\text{Im}(\phi)]^2 - 1\}}, \quad (97)$$

and n is a non-negative integer and the capital A denotes the principal value of the inverse cosine function. The value of n is determined from the function s, which is a periodically varying cosine function with respect to frequency. At zero frequency, n is 0. Every time s cycles through π radians (180 degrees), n is increased by 1. When the solution to the real part of α is found, the solution to the imaginary part of α is then written as $$\text{Im}(\alpha) = \frac{1}{h}\log_e\left\{\frac{\text{Re}(\phi)}{\cos[\text{Re}(\alpha)h]} - \frac{\text{Im}(\phi)}{\sin[\text{Re}(\alpha)h]}\right\}. \quad (98)$$

The real and imaginary parts of a from equations (96) and (98) respectively are combined to yield the complex wavenumber. Because this measurement is made at zero wavenumber ($k_x$=0), this is equal to the dilatational wavenumber. Thus, the dilatational wavespeed is equal to $$c_d = \frac{\omega}{[\text{Re}(\alpha) + i\text{Im}(\alpha)]}. \quad (99)$$

To solve for the shear wavespeed, the specimen must be excited at a nonzero wavenumber. This is done in the next section.

The second part of the measurement method involves insonifying three separate pieces of the material at nonzero wavenumber. The second piece of material is twice as thick as the first piece of material, and the third piece of material is three times as thick as the first piece of material. For nonzero wavenumber, the equations corresponding to the three pieces is $$T_{ba}(k_x, \omega) = \frac{U_z(k_x, b, \omega)}{U_z(k_x, a, \omega)}, \quad (100)$$
$$= \frac{\sin(\alpha a)\cos(\beta a) + [M(k_x, \omega)\cos(\alpha a) + N(k_x, \omega)\sin(\alpha a)]\sin(\beta a)}{\sin(\alpha a) + M(k_x, \omega)\sin(\beta a)}$$
$$= R_1(\omega)$$

$$T_{b2a}(k_x, \omega) = \frac{U_z(k_x, b, \omega)}{U_z(k_x, 2a, \omega)}, \quad (101)$$
$$= \frac{\sin(2\alpha a)\cos(2\beta a) + [M(k_x, \omega)\cos(2\alpha a) + N(k_x, \omega)\sin(2\alpha a)]\sin(2\beta a)}{\sin(2\alpha a) + M(k_x, \omega)\sin(2\beta a)}$$
$$= R_2(\omega)$$

$$T_{b3a}(k_x, \omega) = \frac{U_z(k_x, b, \omega)}{U_z(k_x, 3a, \omega)}, \quad (102)$$
$$= \frac{\sin(3\alpha a)\cos(3\beta a) + [M(k_x, \omega)\cos(3\alpha a) + N(k_x, \omega)\sin(3\alpha a)]\sin(3\beta a)}{\sin(3\alpha a) + M(k_x, \omega)\sin(3\beta a)}$$
$$= R_3(\omega)$$

It is noted that the α and β wavenumbers have different values when compared to the previous section due to their modification by the nonzero spatial wavenumber $k_x$. This dependency is shown in equations (28) and (31). Equations (100), (101), and (102) are now combined, the constants M and N are condensed out, and the sine and cosine terms are reduced using multiple angle trigonometric expressions. Additionally, it is noted that $$\cos(\beta a) = \cos(\alpha a) \quad (103)$$

is one of the solutions to the resulting expression and this term is factored out because it is extraneous. This results in $$U(k_x,\omega)\cos^2(\beta h)+V(k_x,\omega)\cos(\beta h)+W(k_x,\omega)=0, \quad (104)$$

where the constants U, V, and W, are, written with the wavenumber and frequency dependence suppressed, equal to $$U=4R_1[4R_2\cos^2(\alpha a)-2R_3\cos(\alpha a)-R_2-1], \quad (105)$$

$$V=2[-2R_1\cos(\alpha a)+R_2+1/2R_3\cos(\alpha a)+1], \quad (106)$$

and $$W=(R_2+1)[-4R_1\cos^2(\alpha a)+2\cos(\alpha a)+R_1+R_3]. \quad (107)$$

where $\alpha$ was determined with equation (28) using the values of $c_d$ calculated in the previous section. Equation (104) can be solved as $$\cos(\beta h) = \frac{-V + \sqrt{V^2 - 4UW}}{2U} = \varphi_+, \quad (108)$$

and $$\cos(\beta h) = \frac{-V - \sqrt{V^2 - 4UW}}{2U} = \varphi_-, \quad (109)$$

where $\varphi_+$ and $\varphi_-$ are typically a complex valued numbers. Two values of $\varphi$ are present but only one is the correct number. At zero (and very low) frequency, the $\varphi$ value closest to unity is the correct one to use. As frequency increases, every time the angle of the discriminant in equation (108) passes through $\pi$ radians, the value of $\varphi$ changes from equation (108) to equation (109) or vice versa. Once the correct value of $\varphi$ is known, equation (108) or (109) can be expanded into real and imaginary parts and solved, resulting in a value for $\beta$ at every frequency in which a measurement is made. The solution to the real part of $\beta$ is $$\text{Re}(\beta) = \begin{cases} \frac{1}{2h}\text{Arccos}(r) + \frac{m\pi}{2h} m\,\text{even} \\ \frac{1}{2h}\text{Arccos}(-r) + \frac{m\pi}{2h} m\,\text{odd} \end{cases}, \quad (110)$$

where $$r = [\text{Re}(\varphi)]^2 + [\text{Im}(\varphi)]^2 - \sqrt{\{[\text{Re}(\varphi)]^2 + [\text{Im}(\varphi)]^2\}^2 - \{2[\text{Re}(\varphi)]^2 - 2[\text{Im}(\varphi)]^2 - 1\}}, \quad (111)$$

and m is a non-negative integer and the capital A denotes the principal value of the inverse cosine function. The value of m is determined from the function r, which is a periodically varying cosine function with respect to frequency. At zero frequency, m is 0. Every time r cycles through $\pi$ radians (180 degrees), m is increased by 1. When the solution to the real part of $\beta$ is found, the solution to the imaginary part of $\beta$ is then written as $$\text{Im}(\beta) = \frac{1}{h}\log_e\left\{\frac{\text{Re}(\varphi)}{\cos[\text{Re}(\beta)h]} - \frac{\text{Im}(\varphi)}{\sin[\text{Re}(\beta)h]}\right\}. \quad (112)$$

The real and imaginary parts of $\beta$ from equations (110) and (112) respectively are combined to yield the complex wavenumber. Because this measurement is made at nonzero wavenumber, this has to be modified by the spatial wavenumber $k_x$ to calculate the shear wavenumber. This equation is $$k_s = \sqrt{\beta^2 + k_x^2}. \quad (113)$$

The shear wavespeed is then calculated using $$c_s = \frac{\omega}{k_s}. \quad (114)$$

Once the dilatational and shear wavespeeds are known, the Lamé constants or Young's modulus, shear modulus, and Poisson's ratio can also be calculated. A numerical example of all these calculations is included below.

The above measurement method can be simulated by means of a numerical example. Soft rubber-like material properties are used in this simulation. The material has a Young's modulus E of $\{1e7(1-0.20i)[1+(1e-4)f]\}\text{N/m}^2$ where f is frequency in Hz, Poisson's ratio $\upsilon$ equal to 0.45 (dimensionless), and a density of $\rho$ equal to 1200 kg/m$^3$. The base thickness of the material h is 0.01 m, the other transfer functions (subscripts 2 and 3) are calculated using two and three times this value. The water has a density $\rho_f$ of 1025 kg/m$^3$ and a compressional (acoustic) wave velocity of $c_f$ of 1500 m/s. All other parameters can be calculated from these values.

Figure 3A:
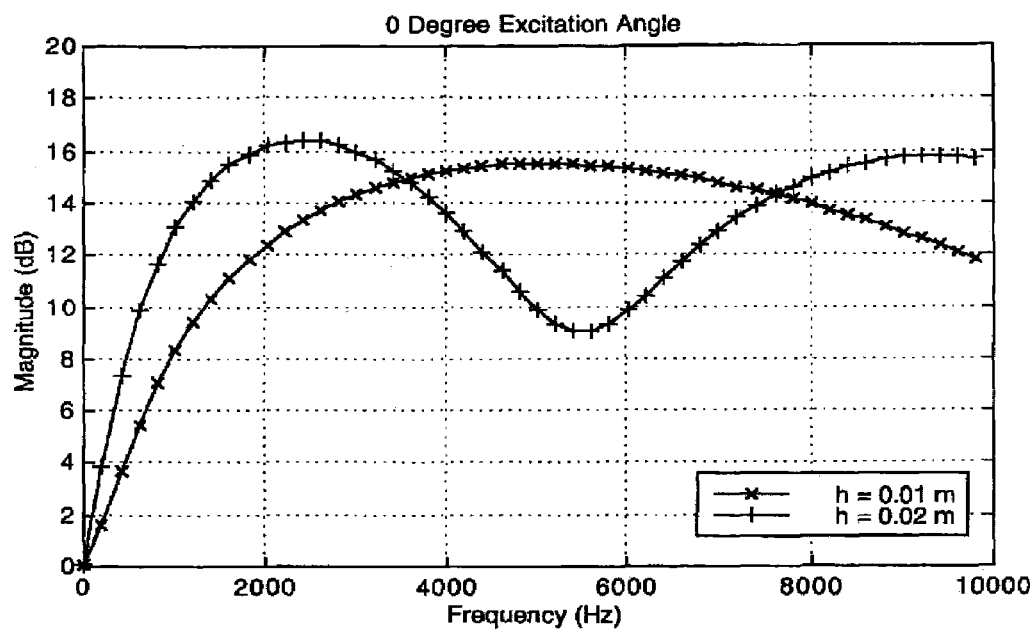
FIGS. 3A and 3B are graphs of the transfer frequency magnitude and phase angle at a zero degree excitation angle.
Figure 3B:
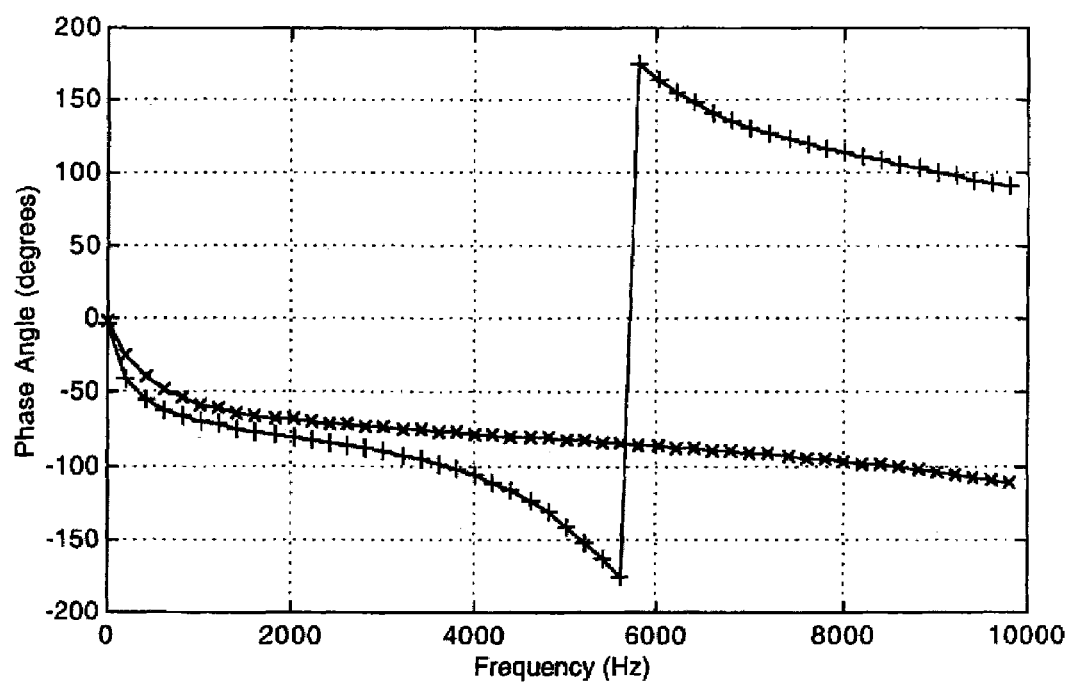
Figure 4:
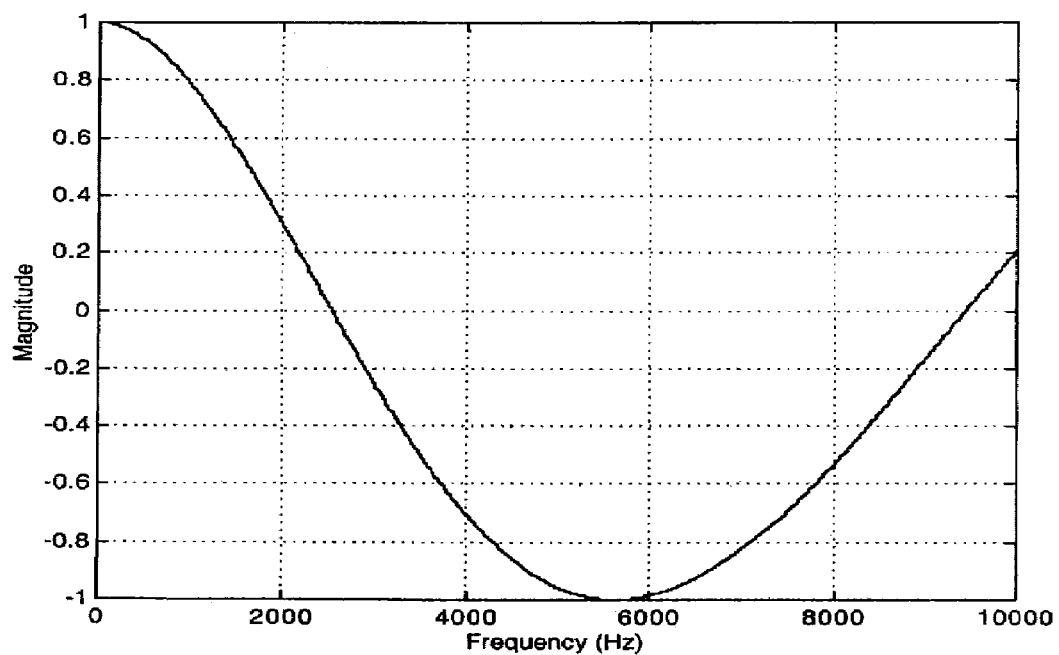
FIG. 4 is a graph of the function s versus frequency.

FIGS. 3A and 3B are plots of transfer function of normal wall motion at z=b divided by normal wall motion at z=a versus frequency at zero wavenumber ($\theta=0°$). The x's correspond to h=0.01 m thickness and the +'s correspond to h=0.02 m thickness. FIG. 3A is the magnitude, and FIG. 3B is the phase angle. These functions are listed above as equations (93) and (94), respectively. FIG. 4 is a plot of the function s versus frequency and corresponds to equation (97). The values of n in equation (96) can be determined from inspection of FIG. 4 and are listed in Table 1, below.

TABLE 1

| n | Minimum Frequency (Hz) | Maximum Frequency (Hz) |
|---|---|---|
| 0 | 0 | 5660 |
| 1 | 5660 | 10000 |

Figure 5A:
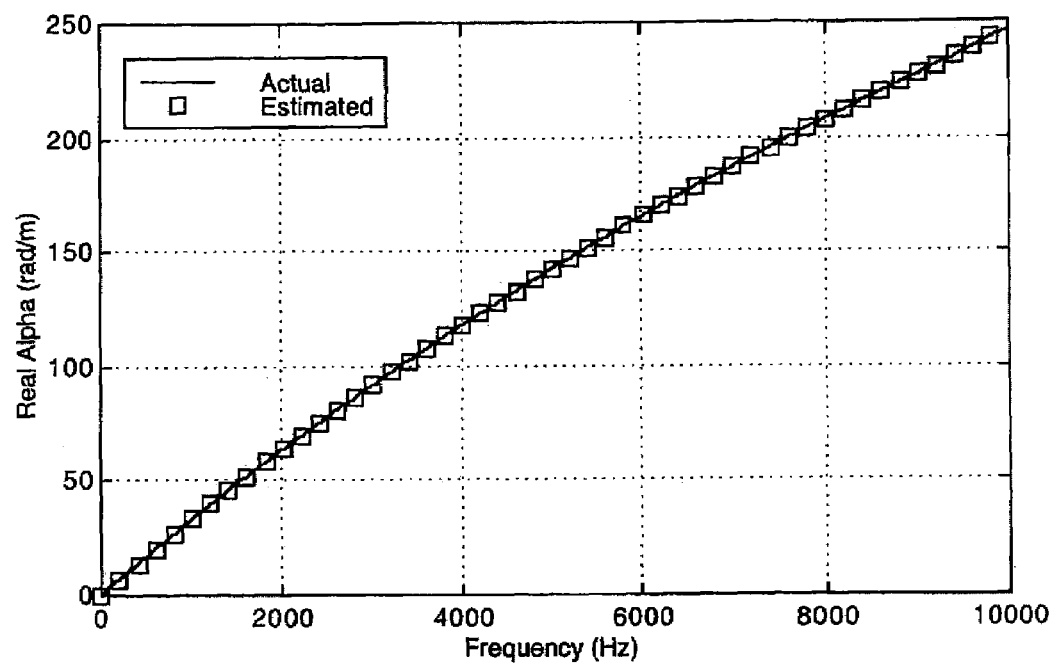
FIGS. 5A and 5B are graphs of the real and imaginary portions of the actual and estimated wavenumber alpha versus frequency.
Figure 5B:
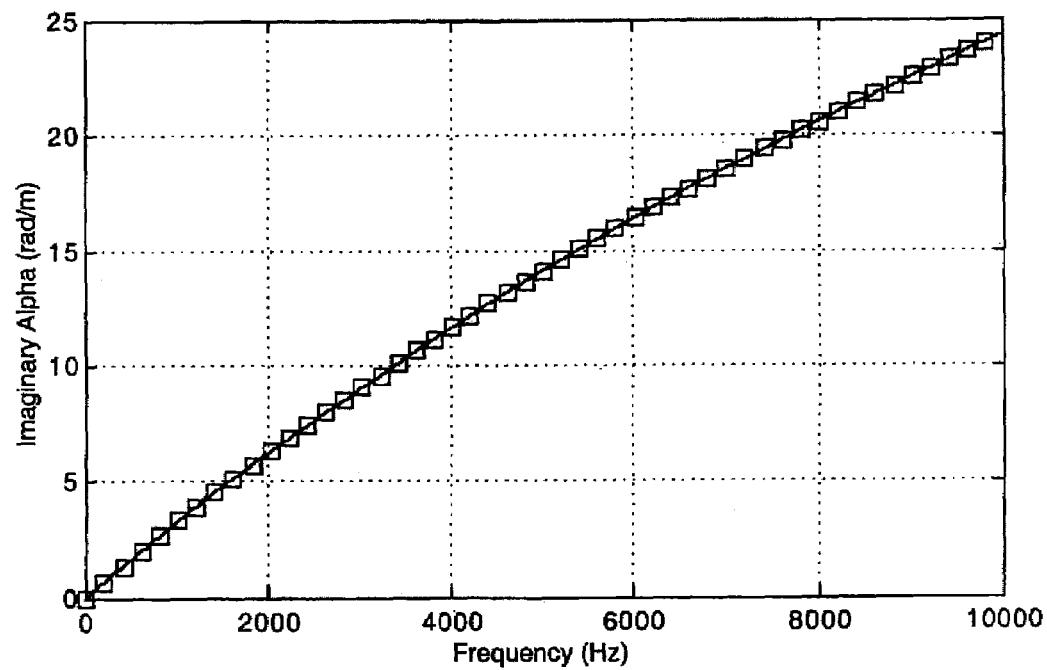
Figure 6A:
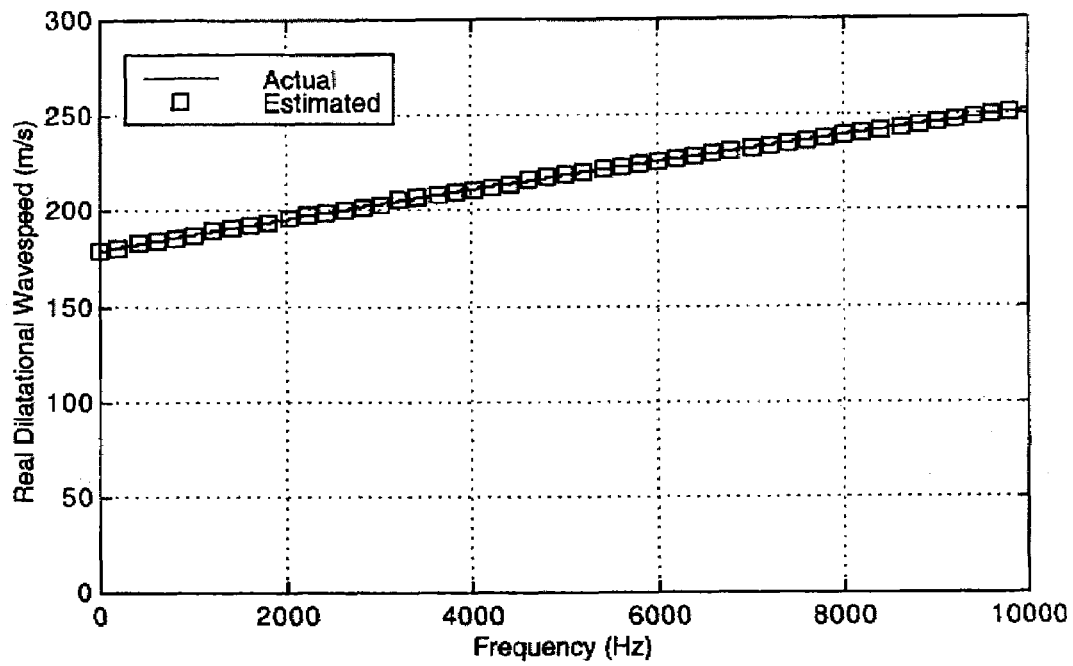
FIGS. 6A and 6B are graphs of the real and imaginary portions of the actual and estimated dilatational wavespeed versus frequency.
Figure 6B:
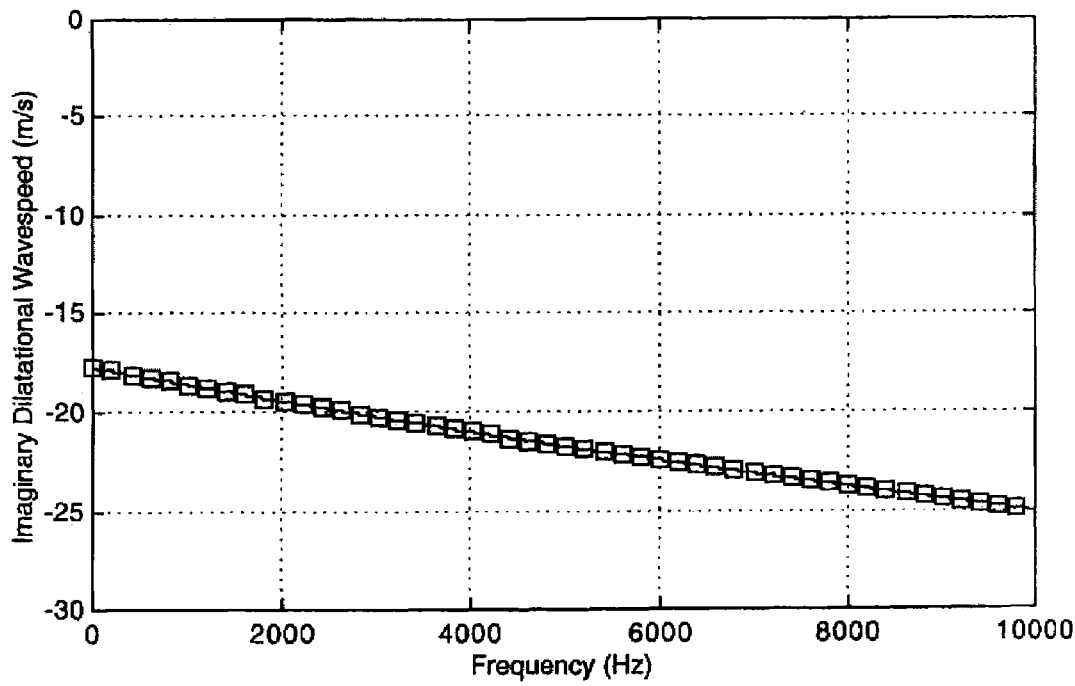

FIGS. 5A and 5B are plots of the actual and estimated values of wavenumber a versus frequency. FIG. 5A is the real part, and FIG. 5B is the imaginary part. The actual values are shown with a solid line and the estimated values are depicted with square markers. FIGS. 6A and 6B are plots of the actual and estimated values of dilatational wavespeed versus frequency. FIG. 6A is the real part, and FIG. 6B is the imaginary part. The actual values are shown with a solid line and the estimated values are depicted with square markers.

Figure 7A:
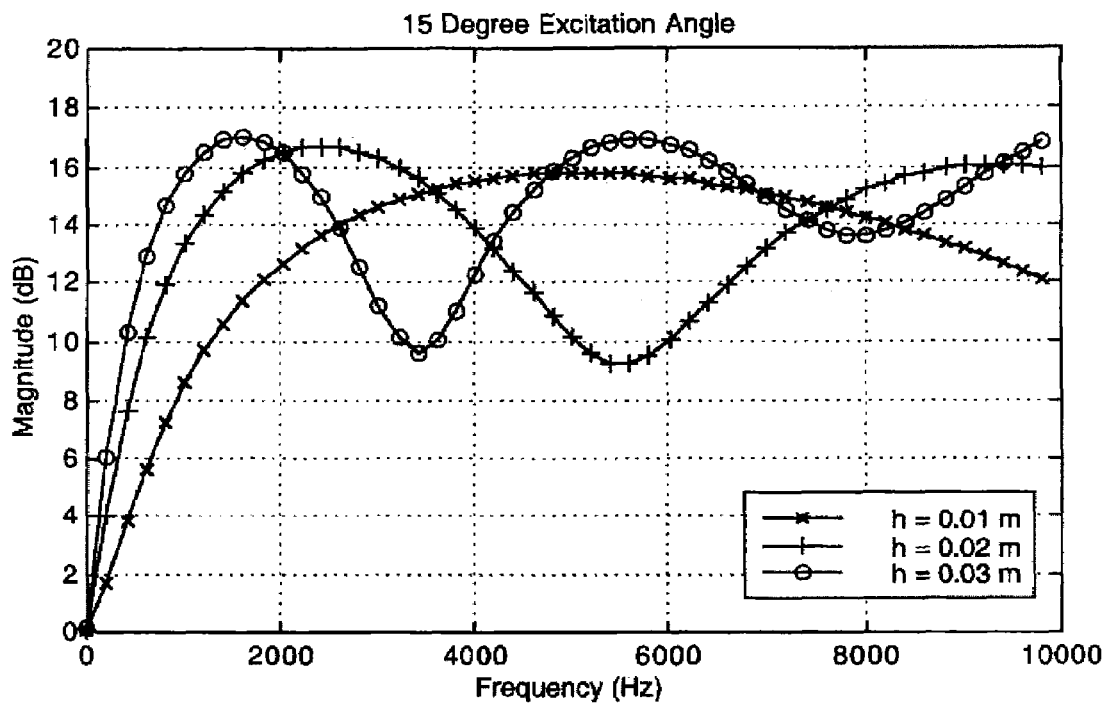
FIGS. 7A and 7B are graphs of the transfer frequency magnitude and phase angle at a fifteen degree excitation angle.
Figure 7B:
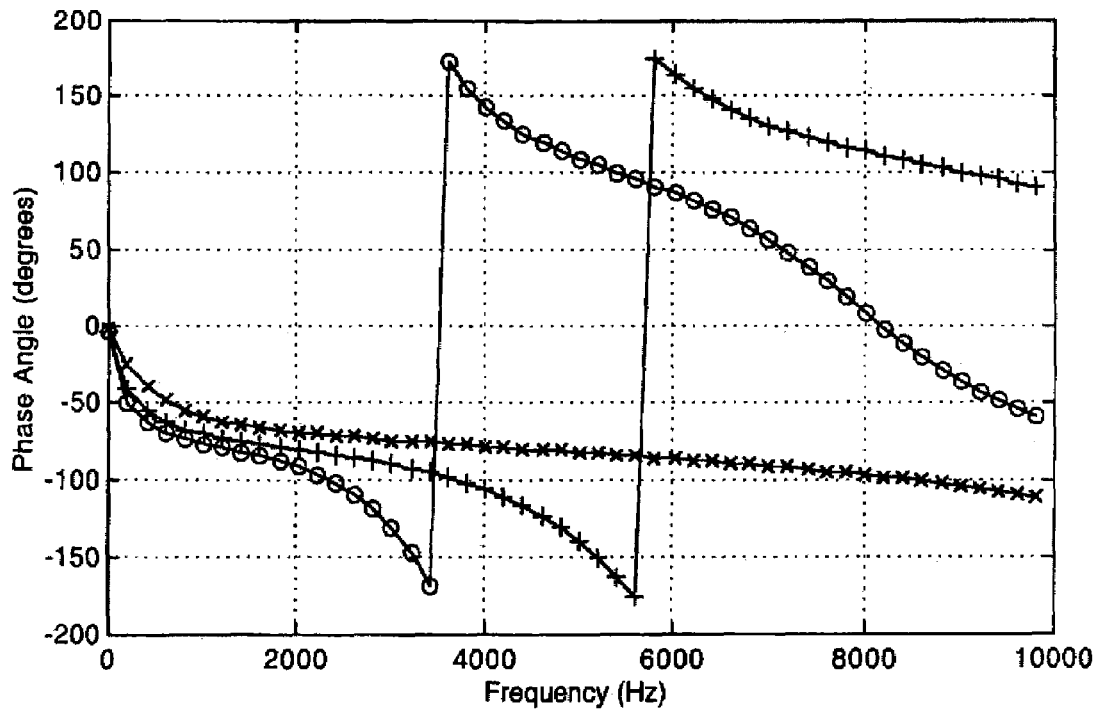
Figure 8:
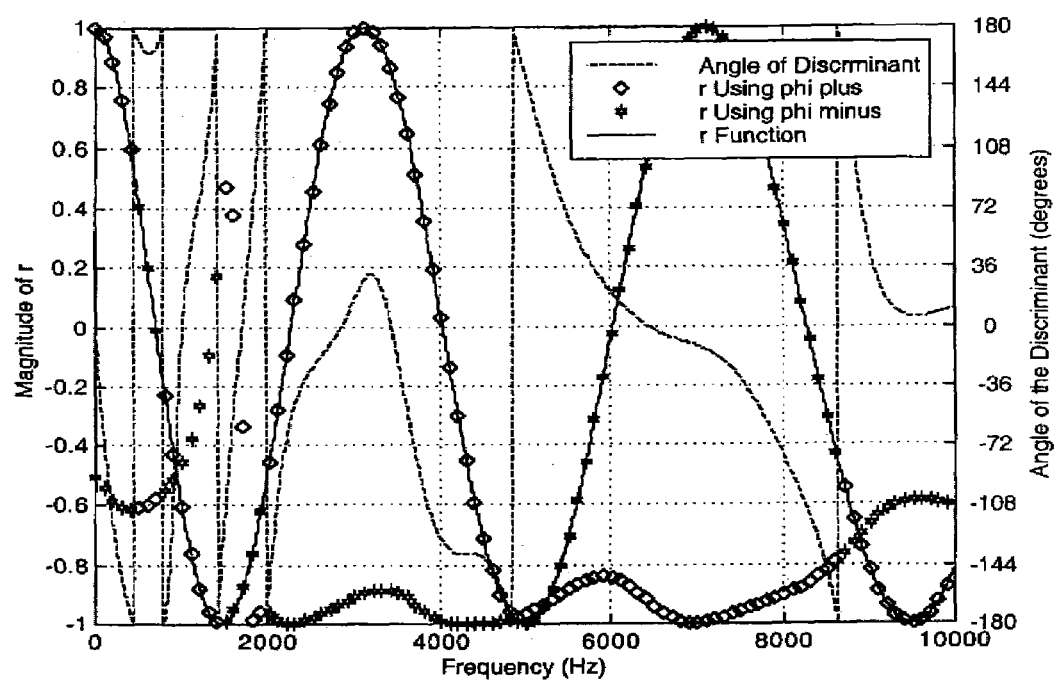
FIG. 8 is a graph of the function r and the angle of the discriminant versus frequency.

FIGS. 7A and 7B are plots of transfer function of normal wall motion at z=b divided by normal wall motion at z=a versus frequency at wavenumbers corresponding to an insonification angle of 15 degrees ($\theta=15+$). The x's correspond to h=0.01 m thickness, the +'s correspond to h=0.02 m thickness, and the o's correspond to h=0.03 m. FIG. 7A is the magnitude, and FIG. 7B is the phase angle. These functions are listed above as equations (100), (101), and (102), respectively. FIG. 8 is a plot of the function r (solid line with markers) and the angle of the discriminant (dashed line) versus frequency and corresponds to equation (111) and (108)

respectively. Also included in this plot is the function r calculated using φ, (equation 108) and .φ_ (equation 109) so that the interchange relationship between these two functions and the discriminant can be illustrated. The values of m in equation (110) can be determined from inspection of FIG. 8 and are listed in Table 2, below.

TABLE 2

| m | Minimum Frequency (Hz) | Maximum Frequency (Hz) |
|---|---|---|
| 0 | 0 | 1460 |
| 1 | 1460 | 3110 |
| 2 | 3110 | 5000 |
| 3 | 5000 | 7120 |
| 4 | 7120 | 9500 |
| 5 | 9500 | 10000 |

Figure 9A:
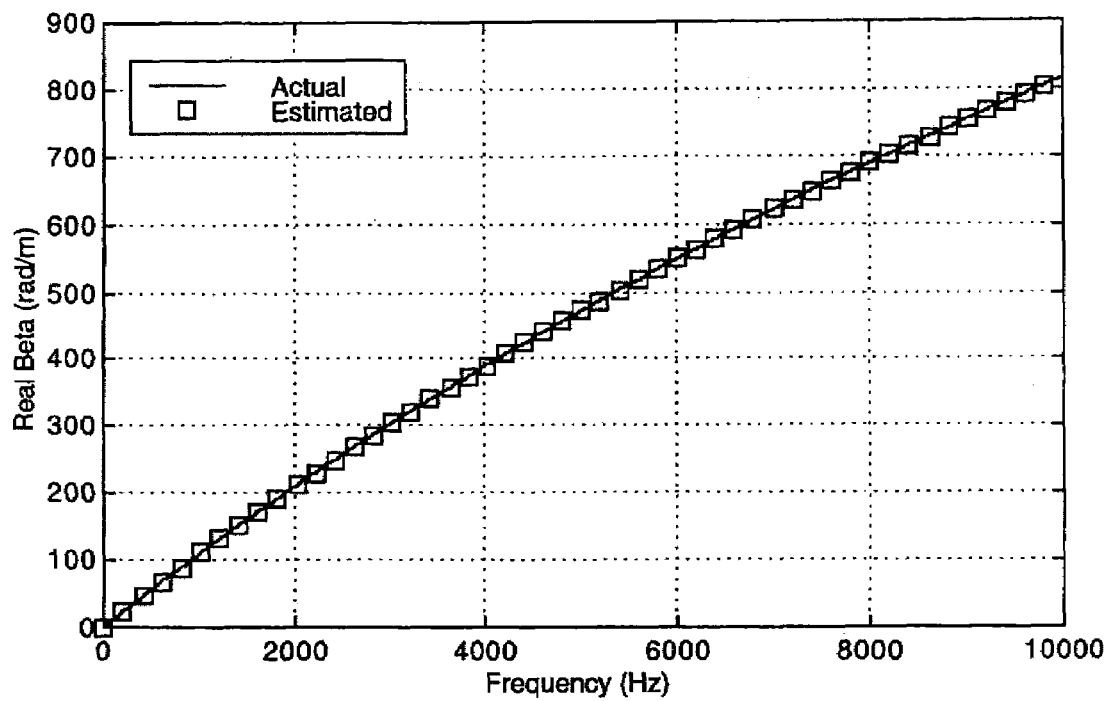
FIGS. 9A and 9B are graphs of the real and imaginary portions of the actual and estimated wavenumber beta versus frequency.
Figure 9B:
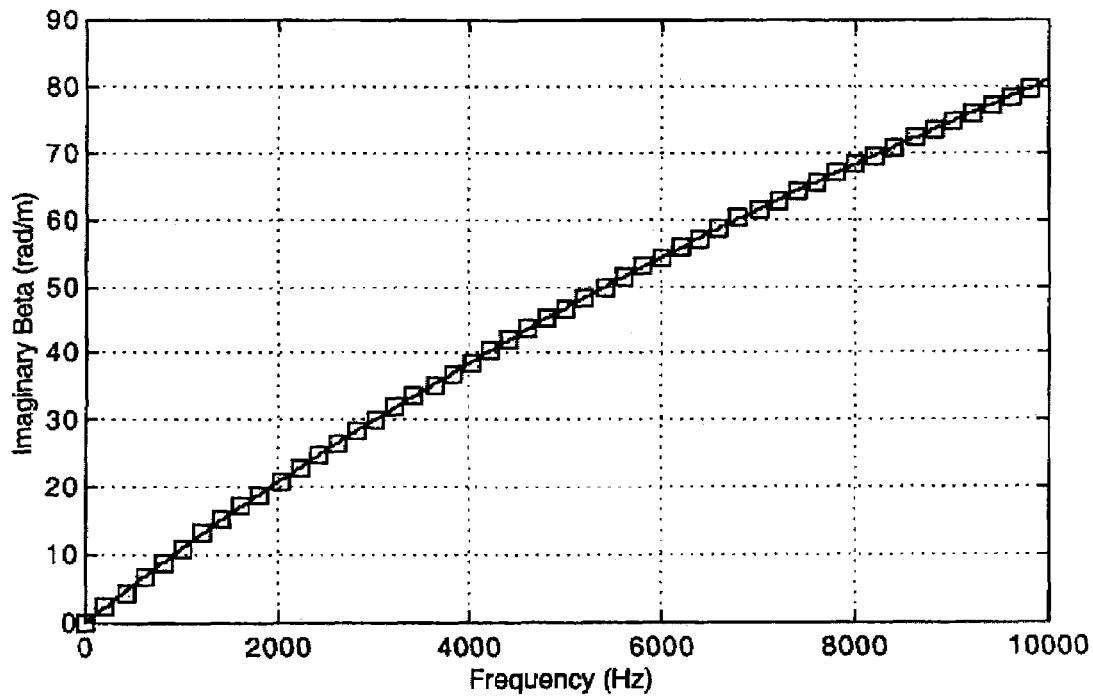
Figure 10A:
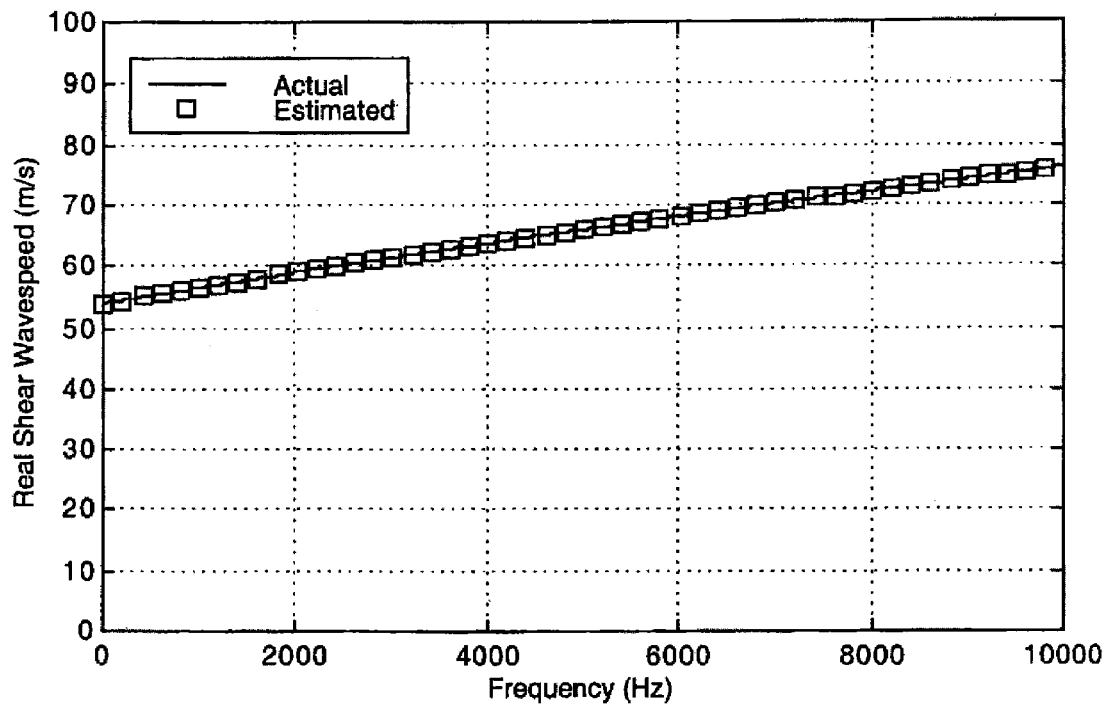
FIGS. 10A and 10B are graphs of the real and imaginary portions of the actual and estimated shear wavespeed versus frequency.
Figure 10B:
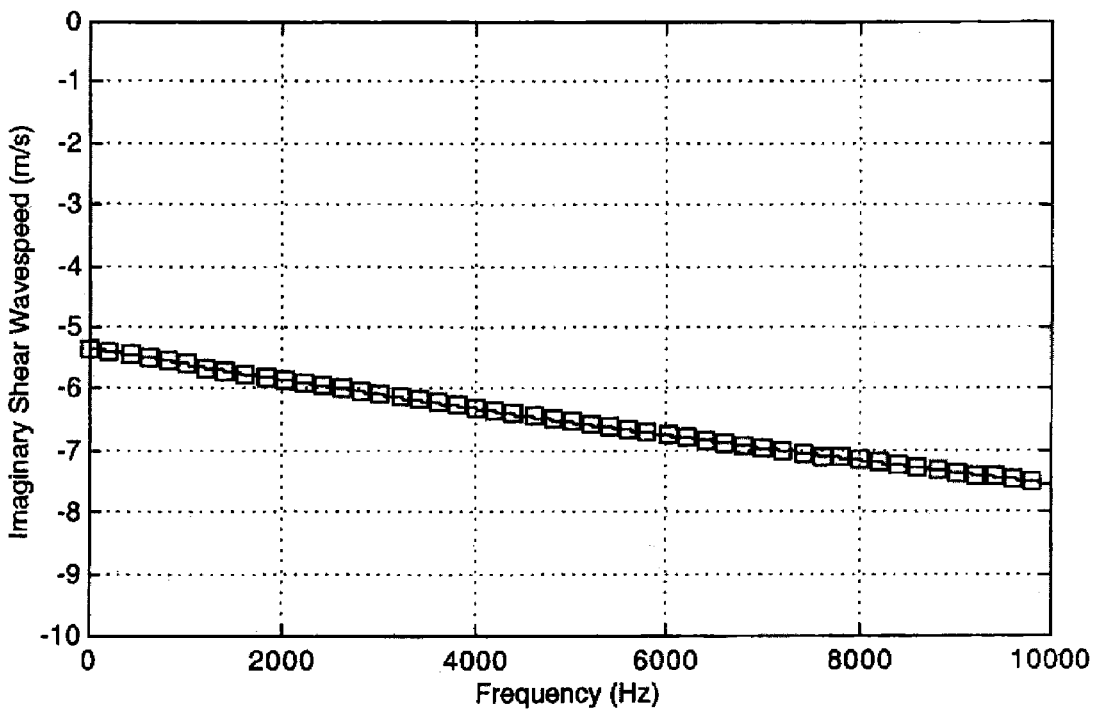

FIGS. 9A and 9B are plots of the actual and estimated values of wavenumber β versus frequency. FIG. 9A is the real part, and FIG. 9B is the imaginary part. The actual values are shown with a solid line and the estimated values are depicted with square markers. FIGS. 10A and 10B are plots of the actual and estimated values of shear wavespeed versus frequency. FIG. 10A is the real part, and FIG. 10B is the imaginary part. The actual values are shown with a solid line and the estimated values are depicted with square markers.

Finally, the material properties can be determined from the wavespeeds. The Lamé constants are calculated with equations (21) and (22) written as $$\mu = \rho c_s^2 \tag{115}$$

and $$\lambda = \rho c_d^2 - 2\rho c_s^2. \tag{116}$$

Figure 11A:
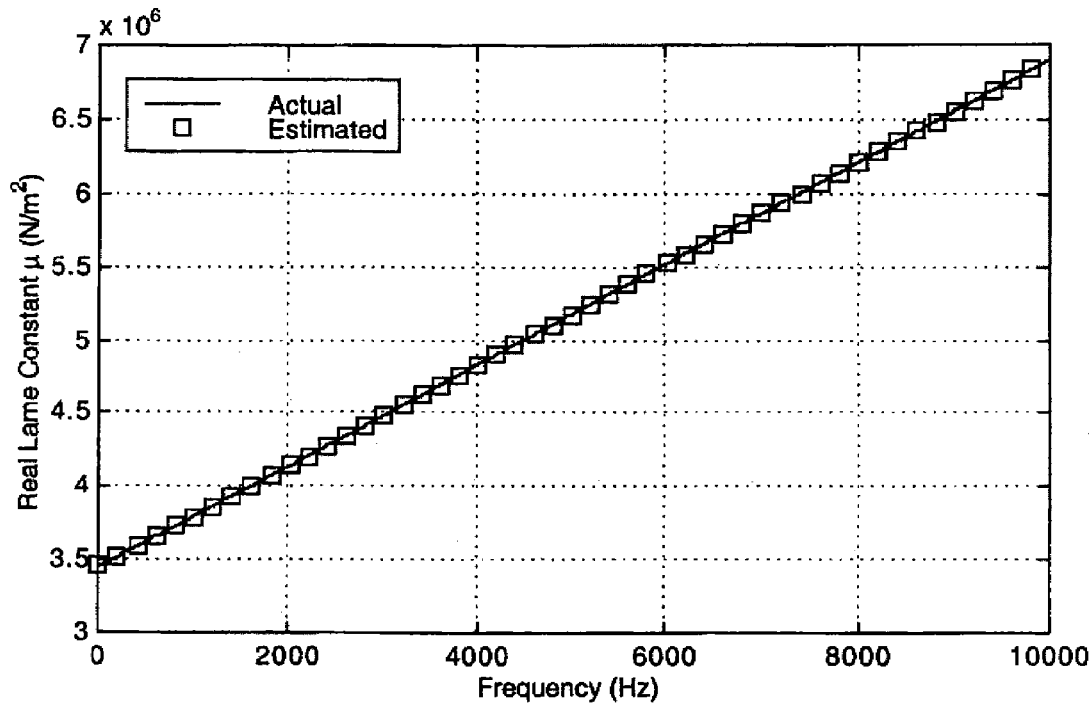
FIGS. 11A and 11B are graphs of the real and imaginary portions of the actual and estimated Lamé constant μ versus frequency.
Figure 11B:
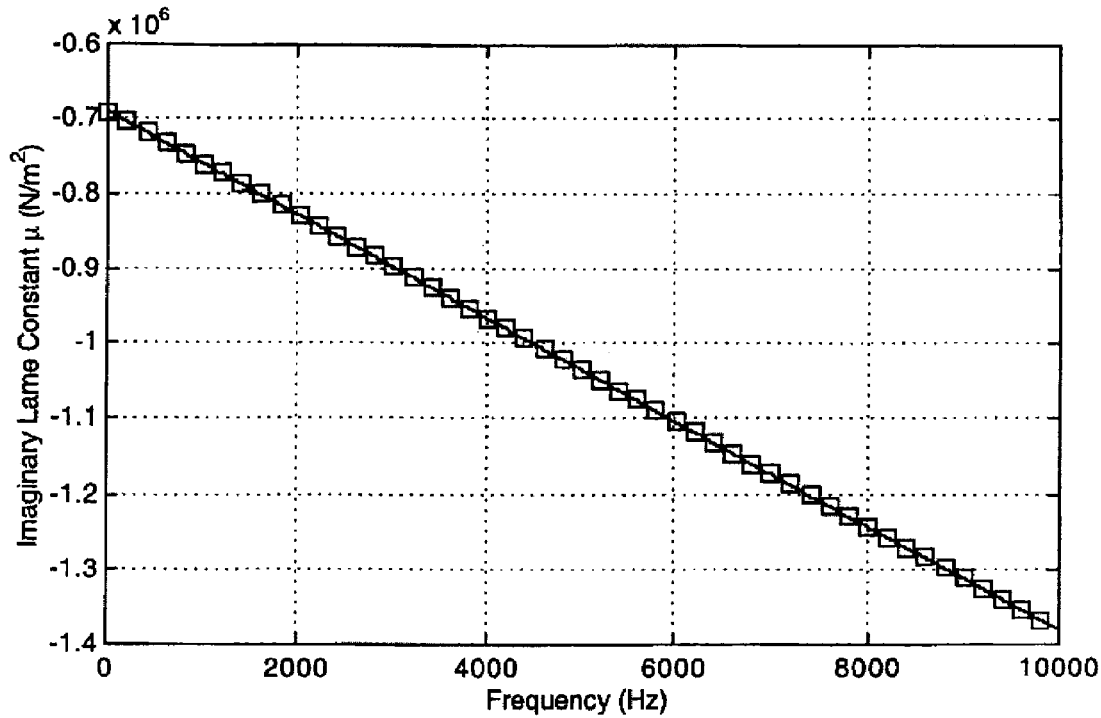
Figure 12A:
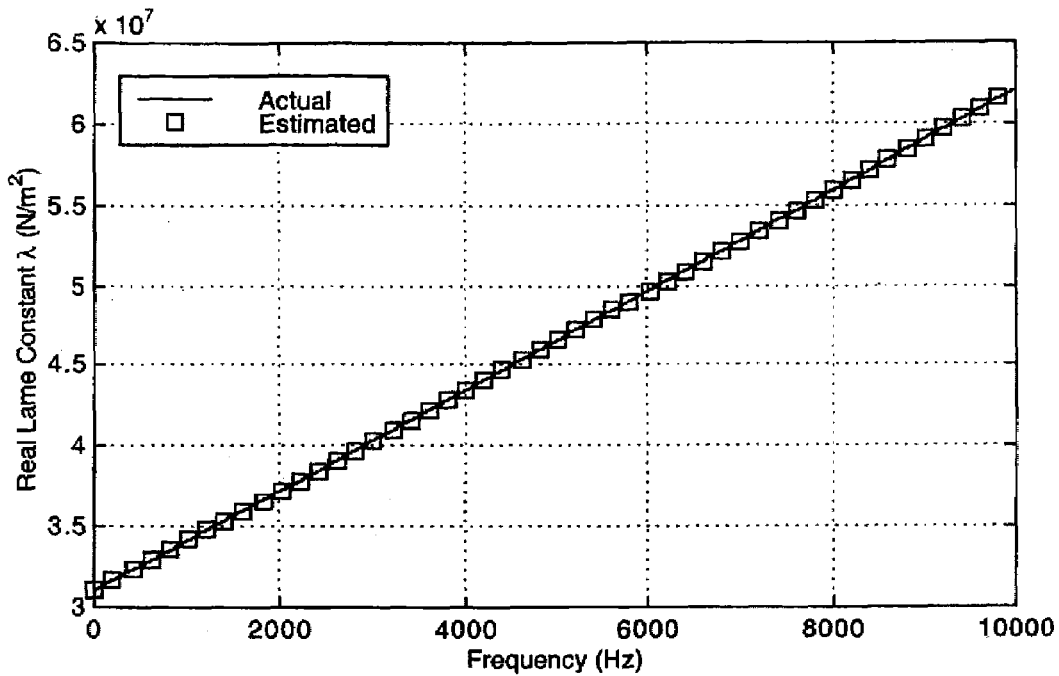
FIGS. 12A and 12B are graphs of the real and imaginary portions of the actual and estimated Lamé constant λ versus frequency.
Figure 12B:
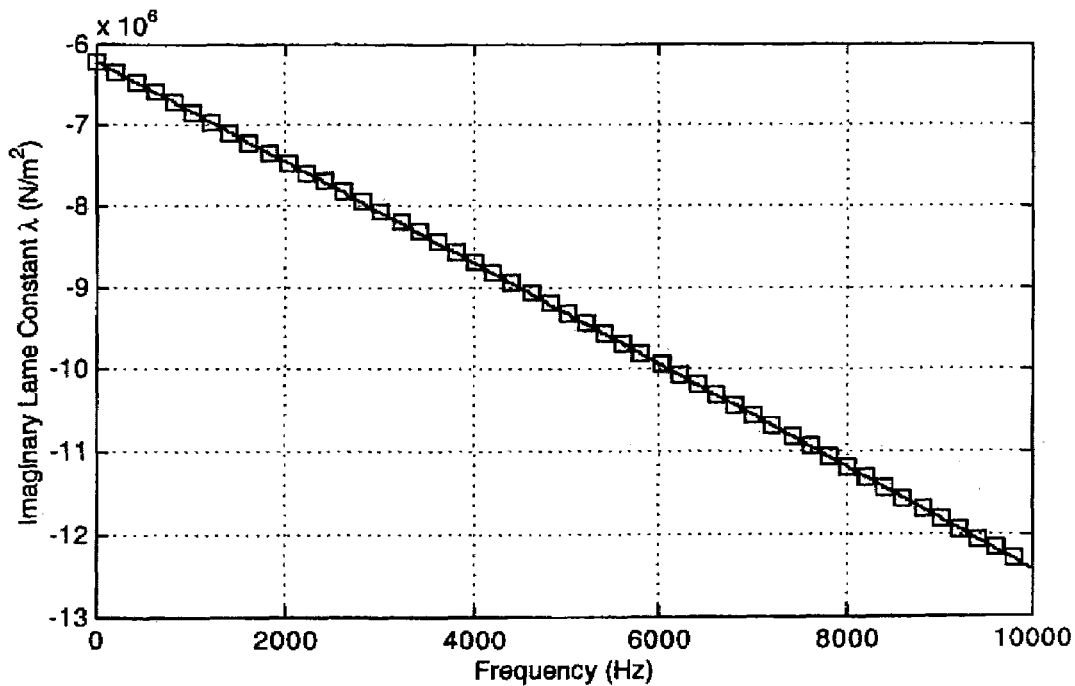
Figure 13A:
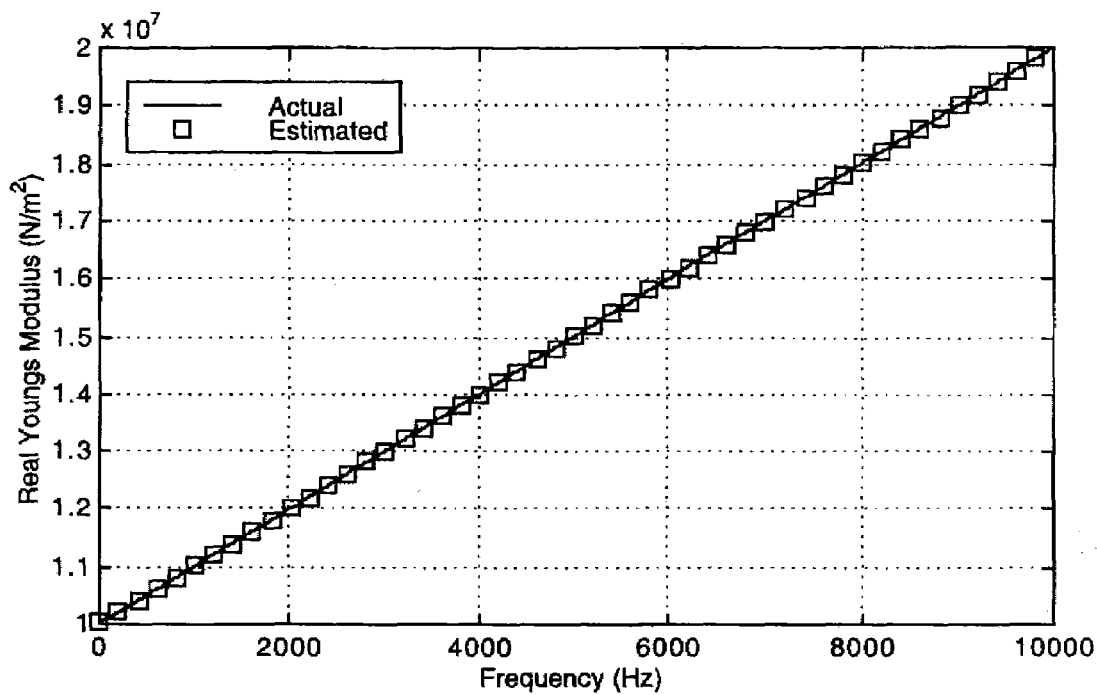
FIGS. 13A and 13B are graphs of the real and imaginary portions of the actual and estimated Young's modulus versus frequency.
Figure 13B:
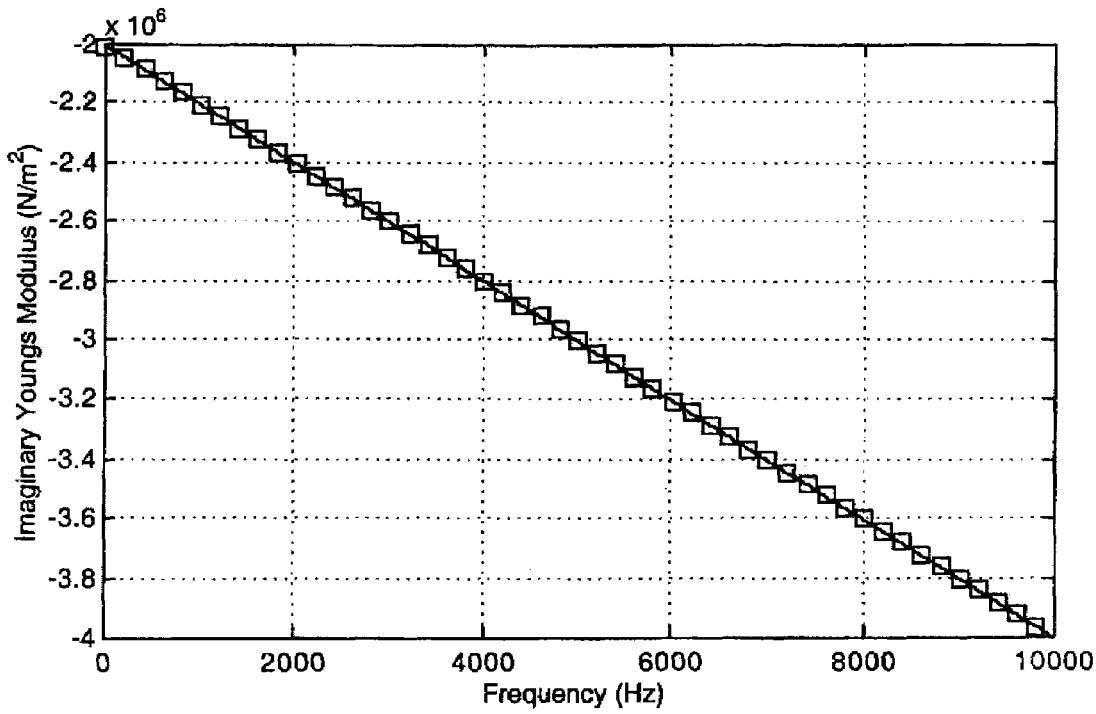

Alternatively, shear modulus, Poisson's ratio, and Young's modulus and can be calculated using equations (23), (24), and (115) which results in $$G \equiv \mu = \rho c_s^2, \tag{117}$$

$$\upsilon = \frac{\lambda}{2(\mu + \lambda)}, \tag{118}$$

and $$E = \frac{2\mu(2\mu + 3\lambda)}{2(\mu + \lambda)}, \tag{119}$$

respectively. FIGS. 11A and 11B are plots of the actual and estimated values of Lamé constant μ versus frequency. FIG. 11A is the real part, and FIG. 11B is the imaginary part. The actual values are shown with a solid line and the estimated values are depicted with square markers. This corresponds to equation (115). FIGS. 12A and 12B are plots of the actual and estimated values of Lamé constant λ versus frequency. FIG. 12A is the real part, and FIG. 12B is the imaginary part. The actual values are shown with a solid line and the estimated values are depicted with square markers. This corresponds to equation (116). The shear modulus G is identical to the Lamé constant μ and therefore is not plotted. Estimation of Poisson's ratio υ yields a value of 0.45 (dimensionless). Because this is a constant with respect to frequency, it is not shown as a figure. FIGS. 13A and 13B are plots of the actual and estimated values of Young's modulus E versus frequency. FIG. 13A is the real part, and FIG. 13B is the imaginary part. The actual values are shown with a solid line and the estimated values are depicted with square markers. This corresponds to equation (119).

In light of the above, it is therefore understood that within the scope of the appended claims, the invention may be practiced otherwise than as specifically described.

What is claimed is:

1. A method for calculating material properties of a material of interest comprising the steps of:
   determining a dilatational wavespeed by:
      conducting an insertion loss test of a first piece of the material having a first thickness at zero wavenumber to obtain first transfer function data;
      conducting an insertion loss test of a second piece of the material having a second thickness at zero wavenumber to obtain second transfer function data, wherein said second thickness is twice said first thickness; and
      calculating the dilatational wavespeed from said first transfer function and said second transfer function;
   determining a shear wavespeed by:
      conducting an insertion loss test of a first piece of the material having a first thickness at a non-zero wavenumber to obtain first shear transfer function data;
      conducting an insertion loss test of a second piece of the material having a second thickness at a non-zero wavenumber to obtain second shear transfer function data, wherein said second thickness is twice said first thickness;
      conducting an insertion loss test of a third piece of the material having a third thickness at zero wavenumber to obtain third shear transfer function data, wherein said third thickness is three times said first thickness;
      calculating the shear wavespeed from said first shear transfer function, said second shear transfer function, said third shear transfer function and said dilatational wavespeed; and
   providing said calculated shear wavespeed and said calculated dilatational wavespeed from said steps of calculating as the material properties.

2. The method of claim 1 wherein said steps of conducting an insertion loss test comprise:
   providing a sample of a material of interest having a first side and a second side;
   providing acoustic energy to said sample on a second side thereof at a selected frequency at an angle selected by reference to the wavenumber;
   measuring a first acceleration of said sample at said first side;
   measuring a second acceleration of said sample at said second side; and
   computing a transfer function as a ratio of said second acceleration to said first acceleration; and
   providing said computed transfer function as one of the material properties.

3. The method of claim 2 wherein said first thickness ranges from 10 mm to 100 mm.

4. The method of claim 2 wherein said steps of measuring a first acceleration and measuring a second acceleration are conducted by utilizing a laser velocimeter.

5. The method of claim 2 wherein said steps of measuring a first acceleration and measuring a second acceleration are conducted by utilizing an accelerometer.

6. The method of claim 2 wherein said insertion loss tests are conducted in a liquid filled housing.

7. The method of claim 2 wherein said insertion loss tests are conducted in a gas filled housing.

8. The method of claim 2 further comprising the step of computing at least one of Lamé constants, Young's modulus, Poisson's ratio, and the shear modulus for the material of interest using said dilatational wavespeed and said shear wave speed.

9. The method of claim 1 wherein said first thickness ranges from 10 mm to 100 mm.

10. The method of claim 1 wherein said insertion loss tests are conducted in a liquid filled housing.

11. The method of claim 1 wherein said insertion loss tests are conducted in a gas filled housing.

12. The method of claim 1 further comprising the step of computing at least one of Lamé constants, Young's modulus, Poisson's ratio, and the shear modulus for the material of interest using said dilatational wavespeed and said shear wave speed.

13. A method for obtaining the dilatational wavespeed of a material comprising the steps of:
   conducting an insertion loss test of a first piece of the material having a first thickness at zero wavenumber to obtain first transfer function data;
   conducting an insertion loss test of a second piece of the material having a first thickness at zero wavenumber to obtain second transfer function data;
   calculating the dilatational wavespeed from said first transfer function and said second transfer function; and
   providing the calculated dilatational wavespeed as one of the material properties.

14. The method of claim 13 wherein said steps of conducting an insertion loss test comprise:
   providing a sample of a material of interest having a first side and a second side;
   providing acoustic energy to said sample on a second side thereof at a selected frequency at an angle selected by reference to the wavenumber;
   measuring a first acceleration of said sample at said first side;
   measuring a second acceleration of said sample at said second side; and
   computing a transfer function as a ratio of said second acceleration to said first acceleration; and
   providing said computed transfer function as one of the material properties.

15. A method for calculating material properties of a material of interest comprising the steps of:
   determining a dilatational wavespeed by:
   conducting an insertion loss test of a first piece of the material having a first thickness at zero wavenumber to obtain first transfer function data;
   conducting an insertion loss test of a second piece of the material having a second thickness at zero wavenumber to obtain second transfer function data, wherein said second thickness is twice said first thickness; and
   calculating the dilatational wavespeed from said first transfer function and said second transfer function;
   determining a shear wavespeed by:
   conducting an insertion loss test of a first piece of the material having a first thickness at a non-zero wavenumber to obtain first shear transfer function data;
   conducting an insertion loss test of a second piece of the material having a second thickness at a non-zero wavenumber to obtain second shear transfer function data, wherein said second thickness is twice said first thickness;
   conducting an insertion loss test of a third piece of the material having a third thickness at zero wavenumber to obtain third shear transfer function data, wherein said third thickness is three times said first thickness;
   calculating the shear wavespeed from said first shear transfer function, said second shear transfer function, said third shear transfer function and said dilatational wavespeed; and
   providing plots of said transfer functions from said steps of conducting insertion loss tests.

16. The method of claim 15 further comprising the steps of:
   computing at least one of Lamé constants and Young's modulus for the material of interest using said dilatational wavespeed and said shear wavespeed; and
   providing a plot of said computed one of Lamé constants and Young's modulus for the material of interest.

17. The method of claim 15 further comprising the step of providing a plot of said dilatational wavespeed versus frequency.

18. The method of claim 15 further comprising the step of providing a plot of said shear wavespeed versus frequency.

* * * * *